United States Patent [19]
Löschberger et al.

[11] Patent Number: 5,814,736
[45] Date of Patent: *Sep. 29, 1998

[54] HOLDER FOR ULTRASONIC TRANSDUCERS

[75] Inventors: Jürgen Löschberger, Fürth; Karl Spendel, Nürnberg; Thomas Siebenhaar, Redwitz; Thomas Möckl, Coburg, all of Germany

[73] Assignee: Siemens Aktiengesellschaft, Munich, Germany

[*] Notice: This patent issued on a continued prosecution application filed under 37 CFR 1.53(d), and is subject to the twenty year patent term provisions of 35 U.S.C. 154(a)(2).

[21] Appl. No.: 734,107

[22] Filed: Oct. 21, 1996

Related U.S. Application Data

[63] Continuation of Ser. No. 734,107, Oct. 21, 1996.

[51] Int. Cl.⁶ ..................................................... G01F 1/66
[52] U.S. Cl. ..................................................... 73/861.25
[58] Field of Search ........................ 73/861.25, 861.26, 73/861.27, 866.5, 617, 632; 128/660.1, 660.09, 662.03

[56] References Cited

U.S. PATENT DOCUMENTS 3,771,117  11/1973  Shaffer et al. ........................ 73/861.27
4,011,473  3/1977  Massa ........................................ 310/8.2
4,593,699  6/1986  Poncy et al. ........................ 128/662.03

FOREIGN PATENT DOCUMENTS 0 260 335 A1  3/1988  European Pat. Off. .
7131858  4/1973  France .
39 41 634 A1  6/1991  Germany .
6-117894  4/1994  Japan ................. 73/861.27
6-117895  4/1994  Japan ................. 73/861.27
6-147946  5/1994  Japan ................. 73/861.27
91/09279  6/1991  WIPO .

*Primary Examiner*—Ronald L. Biegel
*Attorney, Agent, or Firm*—Herbert L. Lerner; Laurence A. Greenberg

[57] ABSTRACT

In ultrasound flow rate meters, an acoustical short circuit between ultrasonic transducers is a special problem. Such a short circuit results in an ultrasonic signal being propagated through a wall of a measuring tube from a sending to a receiving transducer and not being influenced by a medium in the measuring tube. Sealing off a gas path around the ultrasonic transducers is also problematic. In order to solve the problem, the ultrasonic transducers are sheathed with an elastomer molded body. From 25% to 60% of an outer surface of the ultrasonic transducer, which is constructed as a cup-type transducer, is lined with the elastomer molded body, beginning at a cup edge thereof. Contact of the holder with the ultrasonic transducer is minimal and occurs only in an acoustically quiet zone.

11 Claims, 1 Drawing Sheet

HOLDER FOR ULTRASONIC TRANSDUCERS

CROSS-REFERENCE TO RELATED APPLICATION

This application is a continuation of application Ser. No. 08/734,107, filed on Oct. 21, 1996.

BACKGROUND OF THE INVENTION

Field of the Invention

The invention relates to a holder for holding an ultrasonic transducer having a cup-shaped housing with a cup edge facing away from an ultrasound projection direction.

Such a holder is known from German Published, Non-Prosecuted Patent Application DE 39 41 634 A1. In that case, an O-ring is used for the acoustically insulated, exactly positioned holding of an ultrasonic transducer in a flow rate meter. The O-ring is located between linear contacts which are distributed on the principle of a three-point mount. One of the contacts, in the form of a groove, holds the transducer.

Further details of the flow rate meter used therein are described below in conjunction with FIG. 2. The flow rate meter shown in that case for measuring the flow rate of gases and liquids essentially includes a measuring tube that forms a flow conduit for a medium flowing through it and has a rectangular cross section. Two tubular supports, which are offset in the flow direction, are formed obliquely on one of the side walls of the measuring tube, and two ultrasonic transducers are held in them.

Both ultrasonic transducers are operated alternatingly as a sending and a receiving transducer in succession. Whichever ultrasonic transducer is operated as a sending transducer sends an ultrasound signal into the measuring tube, and whichever is the receiving transducer receives the signal, modified by the medium and the speed of the medium in the measuring conduit, after traversing a W-shaped ultrasound path and after triple reflection from the inner walls of the measuring tube.

A special problem in ultrasonic flow rate meters is an acoustical short circuit between the ultrasonic transducers. As a result the ultrasonic signal propagates through the wall of the measuring tube from the sending transducer to the receiving transducer and is not influenced by the medium in the measuring tube. If that signal is received from the receiving transducer and evaluated by the connected electronic unit, it contains no information about the flow. If the signal is mixed with the "genuine" signal, the information about the flow is severely distorted. A solution to the problem resides in minimizing the short-circuit signal, by minimizing the contact between the measuring tube and the transducer.

Another problem in an ultrasonic flow rate meter is sealing off a gas path or flow conduit around the ultrasonic transducers. In some constructions, it is necessary for there to be a direct contact between the medium and the ultrasonic transducer, as FIG. 2 shows. Sealing off the transducers from the measuring tube may be a further task of the transducer holder.

SUMMARY OF THE INVENTION

It is accordingly an object of the invention to provide a holder for holding ultrasonic transducers in a measuring tube, which overcomes or avoids the hereinafore-mentioned disadvantages of the heretofore-known devices of this general type or at least reduces them so that they are unproblematic.

With the foregoing and other objects in view there is provided, in accordance with the invention, a holder for holding an ultrasonic transducer having an ultrasound projection direction and a cup-shaped housing with an outer surface, an outer cup bottom and a cup edge facing away from the ultrasound projection direction, comprising an elastomer molded body sheathing and simultaneously holding the cup-shaped housing, the elastomer molded body beginning at the cup edge and extending over from 25% to 60% of the outer surface of the cup-shaped housing, defining a remainder of the outer surface, the remainder of the outer surface and the outer cup bottom being free of the elastomer molded body.

In accordance with another feature of the invention, the outer surface of the cup-shaped housing has a given jacket height, and there is provided a holding flange disposed on the elastomer molded body and extending beyond the cup edge at the back as seen in the ultrasound projection direction, the holding flange having a mounting surface located in a plane spaced apart from the cup edge by a distance of from 10% to 30% of the given jacket height.

In accordance with a further feature of the invention, the cup-shaped housing has a given outer diameter, and there is provided a holding plate connected to the holding flange and having a circular opening formed therein with a diameter being at least as large as the given outer diameter.

In accordance with an added feature of the invention, the elastomer molded body has a surface facing toward the ultrasound projection direction with an outer edge being rounded or beveled.

In accordance with an additional feature of the invention, the bevel of the surface of the elastomer molded body forms an angle in a range of $45°±15°$.

In accordance with yet another feature of the invention, the cup-shaped housing and the elastomer molded body sheathing the cup-shaped housing have a given widthwise extent; the holding flange holds the cup-shaped housing in a cylinder bore formed in a wall of a measuring tube, the cylinder bore having a given diameter and a cylinder wall; and the given diameter and the given widthwise extent are adapted to one another for preventing the elastomer molded body from touching the cylinder wall in any operating state.

In accordance with yet a further feature of the invention, the molded body is formed of an elastomer having a glass transition point at most equal to 0° C.

In accordance with a concomitant feature of the invention, the molded body is formed of an elastomer having a Shore hardness in the range of 25 to 70.

The holder of the invention has the requisite minimum contact with the measuring tube for the sake of sealing. The contact of the holder with the ultrasonic transducer takes place through the elastomer molded body, in an acoustically quiet zone. The form of the holder is also specified in such a way that no contact between the cylinder wall of the measuring tube and the side wall of the elastomer molded body takes place, over the entire temperature range.

Other features which are considered as characteristic for the invention are set forth in the appended claims.

Although the invention is illustrated and described herein as embodied in a holder for ultrasonic transducers, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 2:
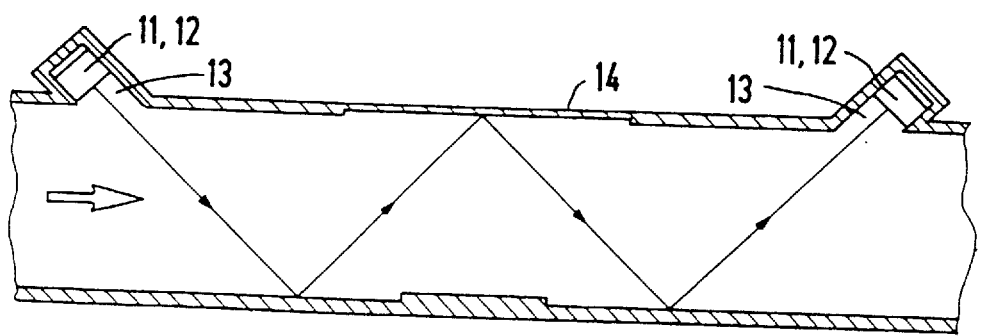
FIG. 2 is a fragmentary, longitudinal-sectional view showing a basic disposition of a flow rate meter of a known type.

Referring now to the figures of the drawings in detail and first, particularly, to FIG. 2 thereof, there is seen a flow rate meter for measuring a flow rate of gases and liquids. The flow rate meter is essentially formed of a measuring tube 14 with a rectangular cross section that forms a flow conduit for a medium flowing through the tube. Two tubular supports, which are offset in a flow direction indicated by an arrow, are formed liquely on the upper side wall of the measuring tube 14 in the view shown in FIG. 2, defining cylinder bores 13. Two ultrasonic transducers 11, 12 are held in the cylinder bores. It can be seen that there is a direct contact between the medium and the ultrasonic transducer in FIG. 2.

The two ultrasonic transducers 11, 12 are operated alternatingly as a sending transducer and a receiving transducer in succession. The ultrasonic transducer that is operated as a sending transducer sends an ultrasound signal into the measuring tube 14, and the receiving transducer receives the signal, modified by the medium and the speed of the medium in the measuring conduit, after traversing a W-shaped ultrasound path shown in FIG. 2 and after triple reflection from the inner walls of the measuring tube 14.

Figure 1:
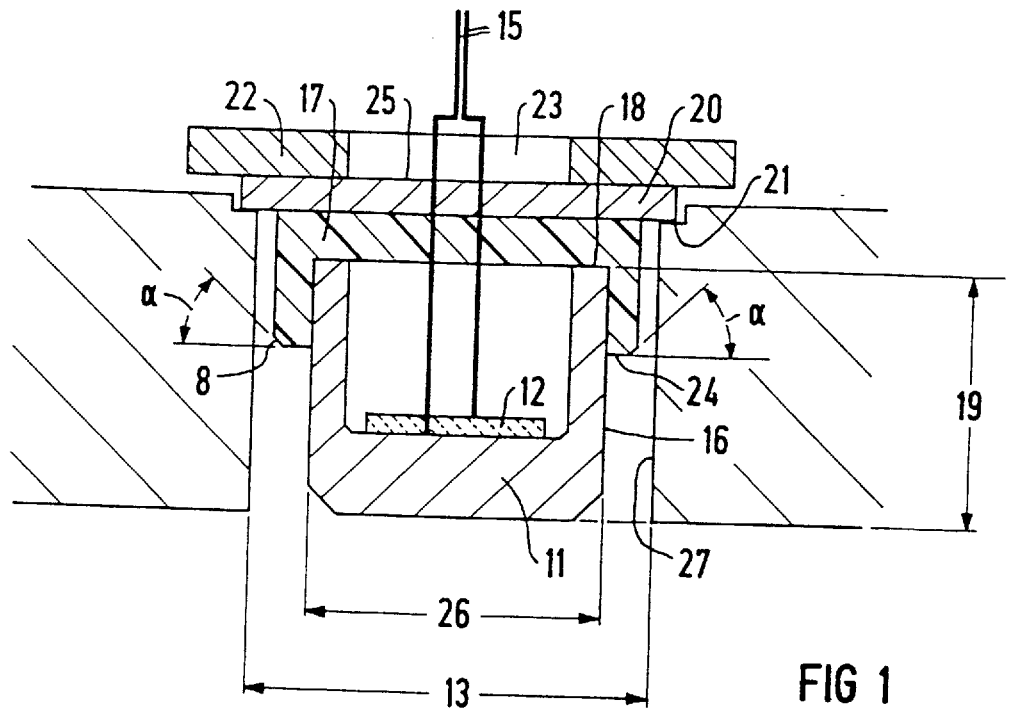
FIG. 1 is a diagrammatic, longitudinal-sectional view of a holder of an ultrasonic transducer in a wall opening of a measuring tube.

FIG. 1 shows a holder of the invention for holding the ultrasonic transducer 11, 12, which is constructed as a cup-type transducer. The holder holds the ultrasonic transducer 11, 12 in the cylinder bore 13 of the measuring tube 14, or of a tubular support formed onto it, of the kind shown in FIG. 2.

The ultrasonic transducer substantially includes a cylindrical cup-shaped housing 11 and a piezoceramic disk 12 which is located on a bottom of a hollow space of the cup-shaped housing 11. An electrical lead 15 is extended to the outside and contacts the piezoceramic disk 12.

An outer or jacket surface 16 of the ultrasonic transducer 11, 12 is closely sheathed on the back, that is in a region shown at the top in FIG. 1, by a cylindrically shaped elastomer molded body 17, which extends past a cup edge 18 of the ultrasonic transducer and lines the outer surface 16 at the back only up to a height in a range of from 25% to 60% of a total surface height 19. The elastomer molded body 17 is parallel and evenly terminated at a distance of at least 10% of the jacket height 19 from the cup edge 18, and there is joined to a holding flange 20. The holding flange 20 has a mounting surface 25 located in a plane that is spaced apart from the cup edge 18 by a distance of from 10% to 30% of the jacket height 19.

The holding flange 20 is oversized as compared with the diameter of the cylinder bore 13 and is supported on the outside of the cylinder bore 13 on a shoulder 21. A disklike holding plate 22 rests on the other side of the holding flange 20 and has a central bore 23 with diameter that should at least be no smaller than an outer diameter 26 of the cup-shaped housing 11. The electric lead 15 of the ultrasonic transducer 11, 12 is extended to the outside through the central bore 23.

The elastomer molded body 17 has a side facing toward an ultrasound projection direction, which is a surface 24 facing downward in FIG. 1, that is rounded or beveled at an outer edge 8 in an angle $\alpha = 45° \pm 15°$. This bevel prevents propagation of a possible natural oscillation of the sheathing and therefore prevents the transmission of such oscillation to the wall of the measuring tube.

The diameter of the cylinder bore 13 of the measuring tube 14, or of the tubular support of FIG. 2 on the measuring tube 14, into which the ultrasonic transducer 11, 12 protrudes, is so great that contact of a cylinder wall 27 by the elastomer molded body 17 is reliably avoided in every operating state, for instance over the entire operating temperature range.

The elastomer of the molded body 17 has a glass transition point of less than or equal to 0° C. and a Shore hardness of 25 to 70. The elastomer is also selected for the property of having an acoustically damping action in the operating frequency range of the ultrasonic transducer 11, 12.

We claim:

1. In a holder for holding an ultrasonic transducer having an ultrasound projection direction and a cup-shaped housing with an outer wall surface, an outer cup bottom and a cup edge facing away from the ultrasound projection direction, the improvement comprising:

an elastomer molded body sheathing and holding the cup-shaped housing in direct contact, said elastomer molded body beginning at the cup edge and extending over from 25% to 60% of the outer surface of the cup-shaped housing, defining a remainder of the outer wall surface, the remainder of the outer surface and the outer cup bottom being free of said elastomer molded body.

2. The holder according to claim 1, wherein the outer surface of the cup-shaped housing has a given jacket height, and including a holding flange disposed on said elastomer molded body and extending beyond the cup edge at the back as seen in the ultrasound projection direction, said holding flange having a mounting surface located in a plane spaced apart from the cup edge by a distance of from 10% to 30% of the given jacket height.

3. The holder according to claim 2, wherein the cup-shaped housing has a given outer diameter, and including a holding plate connected to said holding flange and having a circular opening formed therein with a diameter being at least as large as the given outer diameter.

4. The holder according to claim 1, wherein said elastomer molded body has a surface facing toward the ultrasound projection direction with an outer edge being rounded or beveled.

5. The holder according to claim 4, wherein said bevel of said surface of said elastomer molded body forms an angle in a range of $45° \pm 15°$.

6. The holder according to claim 2, wherein:

the cup-shaped housing and said elastomer molded body sheathing the cup-shaped housing have a given width-wise extent;

said holding flange holds the cup-shaped housing in a cylinder bore formed in a wall of a measuring tube, the cylinder bore having a given diameter and a cylinder wall; and the given diameter and the given widthwise extent are adapted to one another for preventing said elastomer molded body from touching the cylinder wall in any operating state.

7. The holder according to claim 1, wherein said molded body is formed of an elastomer having a glass transition point at most equal to 0° C.

8. The holder according to claim 1, wherein said molded body is formed of an elastomer having a Shore hardness in the range of 25 to 70.

9. An ultrasonic transducer assembly, comprising:

a cup-shaped housing having an outer surface, a cup bottom, a cup wall contiguous with said cup bottom, and a cup edge formed on said cup wall distally from said cup bottom;

an ultrasonic transducer having an ultrasound projection direction, said ultrasonic transducer being disposed in said cup-shaped housing with said ultrasound projection direction oriented through said cup bottom and away from said cup edge;

an elastomer molded body holding said cup-shaped housing in direct contact at said cup edge, said elastomer molded body sheathing said cup wall at the cup edge and leaving a remainder of said cup wall and said cup bottom free of said elastomer molded body.

10. The assembly according to claim 9, wherein said elastomer molded body covers from 25% to 60% of said cup wall of said cup-shaped housing.

11. The assembly according to claim 9, wherein said elastomer molded body is integrally molded onto said cup edge and covers from 25% to 60% of said cup wall of said cup-shaped housing.

\* \* \* \* \*

UNITED STATES PATENT AND TRADEMARK OFFICE
CERTIFICATE OF CORRECTION

PATENT NO. : 5,814,736
DATED : Sept. 29, 1998
INVENTOR(S) : Jurgen Loschberger, et al It is certified that error appears in the above-identified patent and that said Letters Patent is hereby corrected as shown below:

On title page, [63], after "1996" insert --and a continuation of PCT/DE94/00429, Apr. 19, 1994--

Signed and Sealed this

Eighteenth Day of April, 2000

Attest:

Q. TODD DICKINSON

Attesting Officer

Director of Patents and Trademarks